United States Patent [19]
King et al.

[11] Patent Number: 6,090,082
[45] Date of Patent: Jul. 18, 2000

[54] VIAL RETAINER INTERFACE TO A MEDICATION DELIVERY PEN

[75] Inventors: Christopher B. King, Greenwood Lake, N.Y.; James Best, Weehawken; Daniel A. Walters, Rockaway Township, both of N.J.

[73] Assignee: Becton, Dickinson and Company, Franklin Lakes, N.J.

[21] Appl. No.: 09/027,770

[22] Filed: Feb. 23, 1998

[51] Int. Cl.$^7$ .................................................. A61M 5/00
[52] U.S. Cl. ........................................... 604/234; 604/187
[58] Field of Search ................................... 604/181, 187, 604/207–210, 232, 234

[56] References Cited

U.S. PATENT DOCUMENTS

| | | | |
|---|---|---|---|
| 4,592,745 | 6/1986 | Rex et al. ................................. | 604/211 |
| 4,936,833 | 6/1990 | Sams ........................................ | 604/232 |
| 5,114,406 | 5/1992 | Gabriel et al. .......................... | 604/136 |
| 5,226,895 | 7/1993 | Harris ...................................... | 604/208 |
| 5,938,642 | 8/1999 | Burroughs et al. ..................... | 604/208 |

*Primary Examiner*—Wynn Wood Coggins
*Assistant Examiner*—Deborah Blyveis
*Attorney, Agent, or Firm*—Alan W. Fiedler

[57] ABSTRACT

A medication delivery pen having a vial retainer with a side opening have flexible snap wings that spread to receive and retain a standard or threaded vial within the vial retainer. The vial retainer also includes an improved means of attaching the vial retainer to a pen injector body, using a cam and cam follower design together with a ratcheting mechanism to prevent removal of the vial from the medication delivery pen. Alternatively, a release mechanism could be used so that the vial may be removed from the medication delivery pen. In addition, the vial retainer includes an opening for receiving the vial defined by a pair of flexible snap wings.

7 Claims, 8 Drawing Sheets

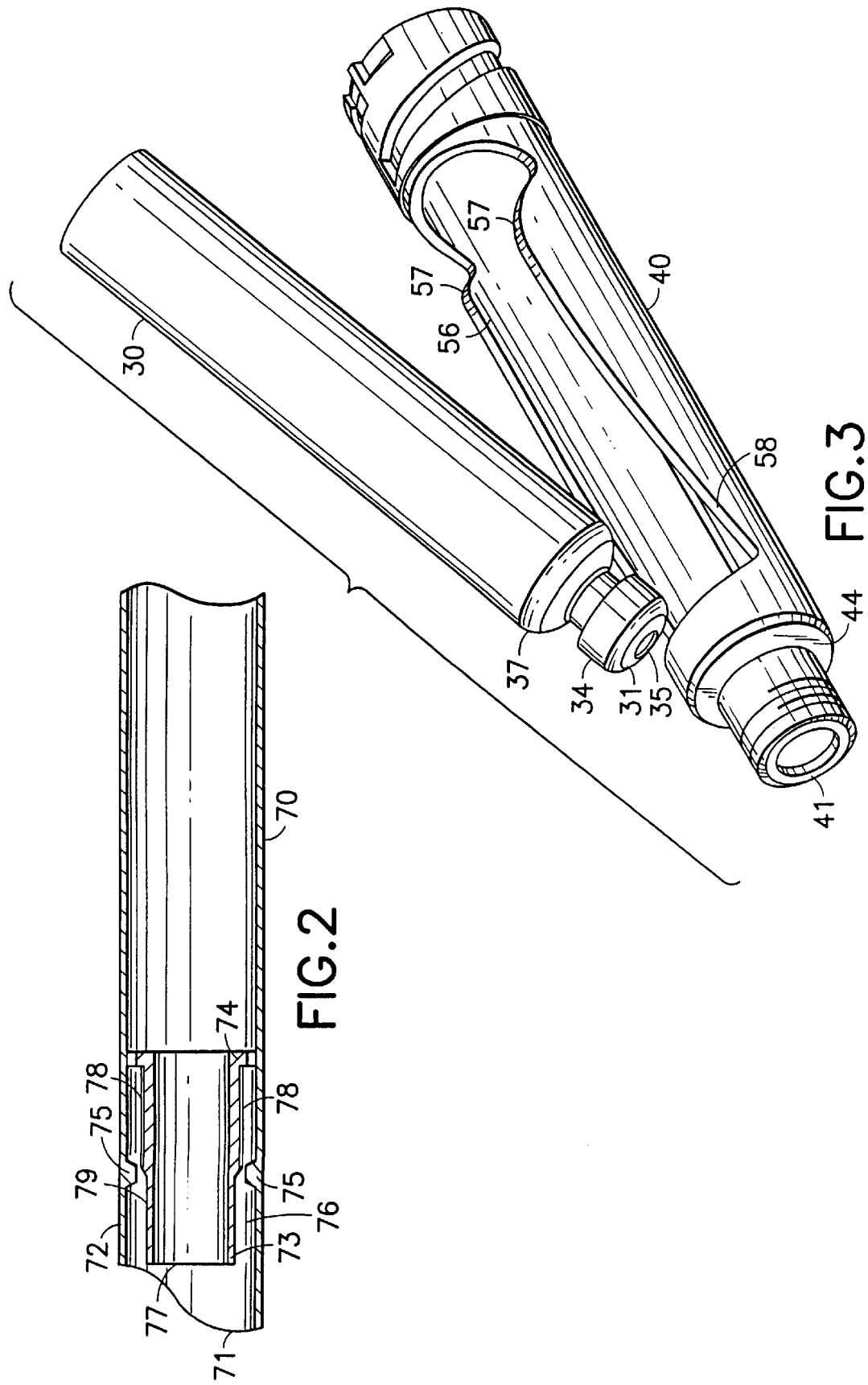

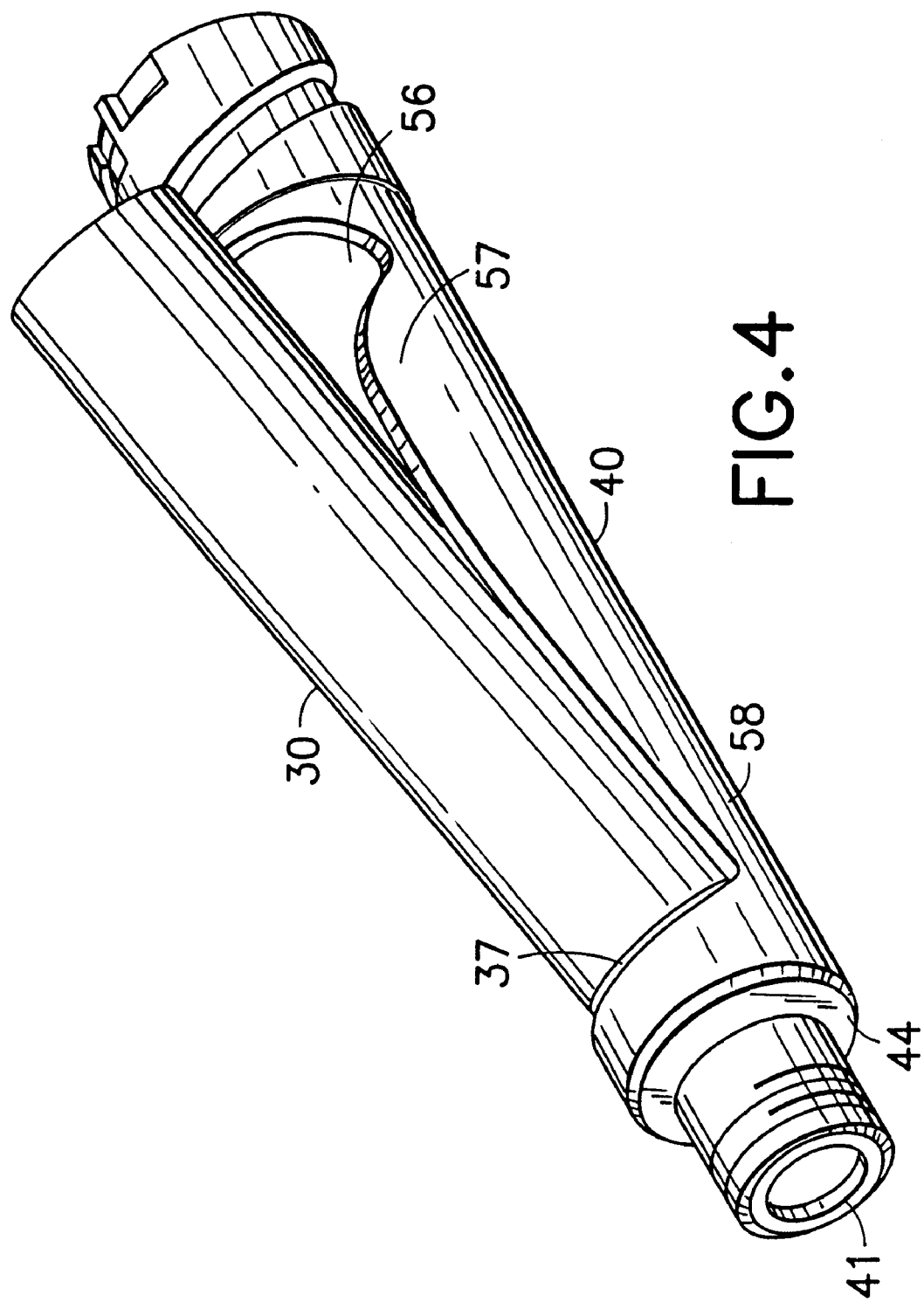

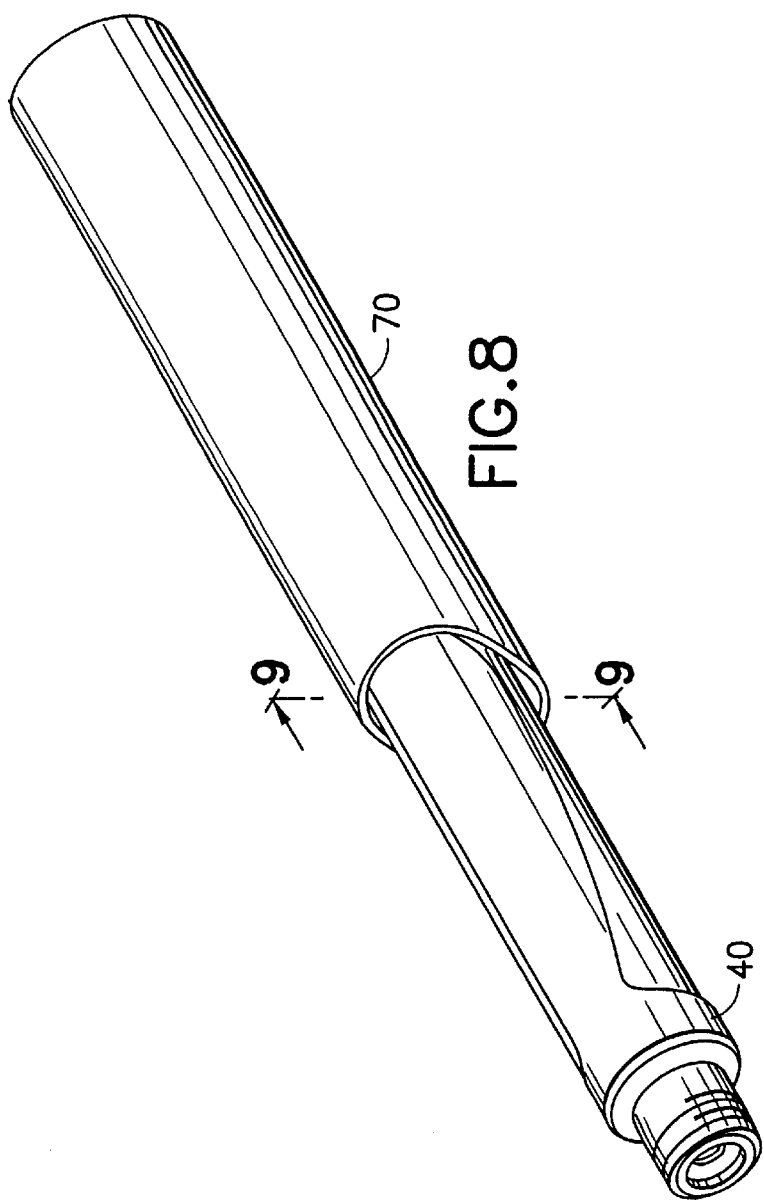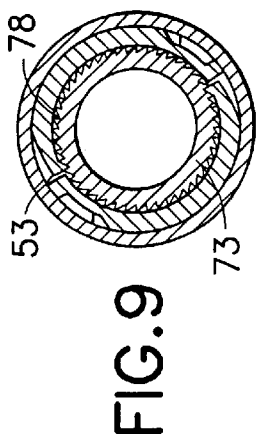

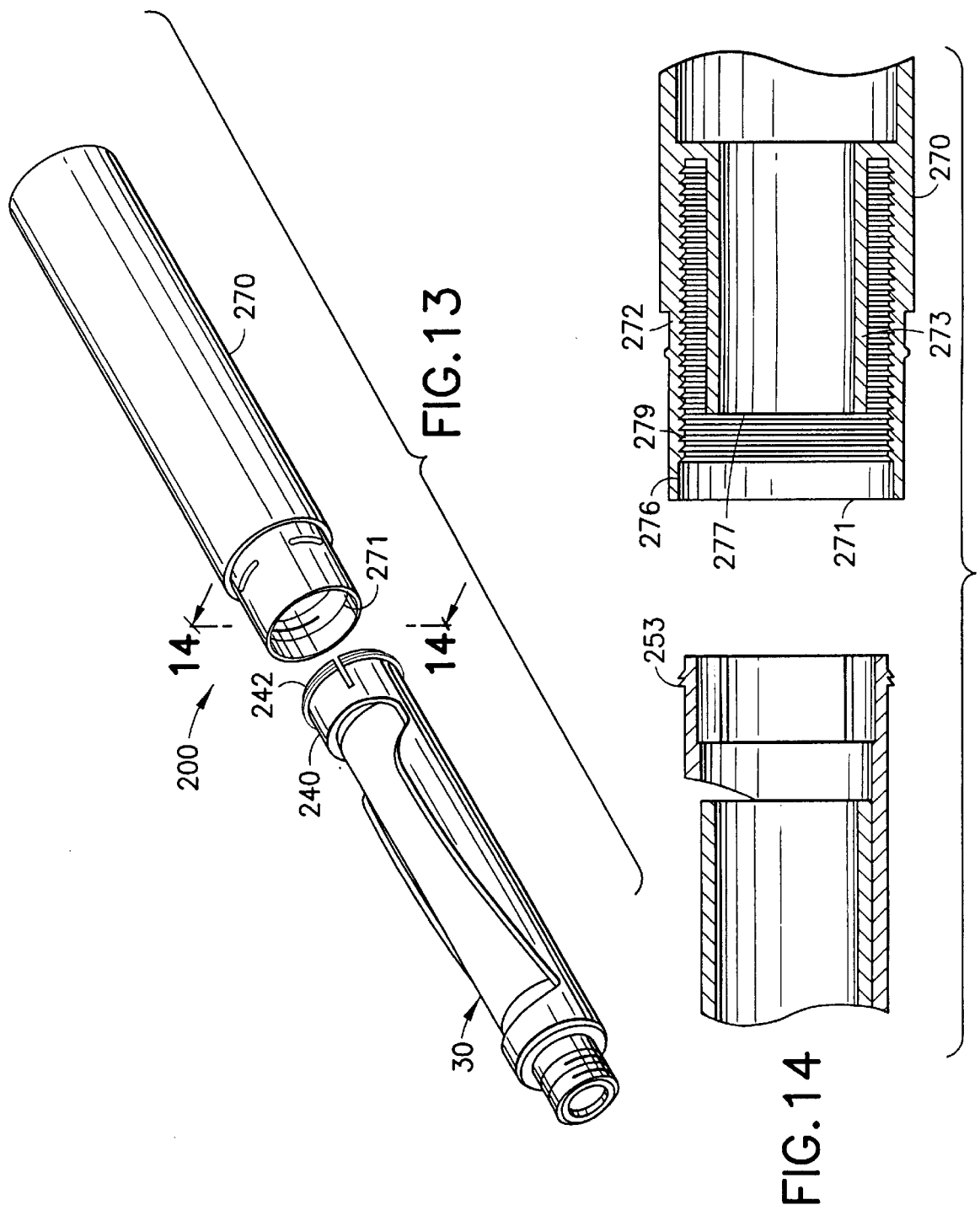

VIAL RETAINER INTERFACE TO A MEDICATION DELIVERY PEN

BACKGROUND OF THE INVENTION

1. Field of the Invention

The present invention relates to a new vial retainer for medication delivery pens having a specially designed opening in the wall of the vial retainer for receiving standard vials or threaded vials and having ratchet-like means for attaching the vial retainer to a pen injector body of the medication delivery pen.

2. Description of Related Art

Hypodermic syringes are used to deliver selected doses of medication to patients. The prior art hypodermic syringe includes a syringe barrel having opposed proximal and distal ends. A cylindrical chamber wall extends between the ends and defines a fluid receiving chamber. The proximal end of the prior art syringe barrel is substantially open and receives a plunger in sliding fluid tight engagement. The distal end of the prior art syringe barrel includes a passage communicating with the chamber. A needle cannula may be mounted to the distal end of the prior art syringe barrel, such that the lumen of the needle cannula communicates with the passage and the chamber of the syringe barrel. Movement of the plunger in a proximal direction draws fluid through the lumen of the needle cannula and into the chamber. Movement of the plunger in a proximal-to-distal direction urges fluid from the chamber and through the lumen of the needle cannula.

Medication to be injected with the prior art hypodermic syringe often is stored in a vial having a pierceable elastomeric seal. Medication in the prior art vial is accessed by piercing the elastomeric seal with the needle cannula. A selected dose of the medication may be drawn into the chamber of the syringe barrel by moving the plunger a selected distance in a proximal direction. The needle cannula may be withdrawn from the vial, and the medication may be injected into a patient by moving the plunger in a distal direction.

Some medication, such as insulin is self-administered. The typical diabetes patient will require injections of insulin several times during the course of the day. The required dose of insulin will vary from patient to patient, and for each patient may vary during the course of the day and from day to day. Each diabetes patient will establish a regimen that is appropriate for his or her own medical condition and for his or her lifestyle. The regimen typically includes some combination of a slow or medium acting insulin and a faster acting insulin. Each of these regimens may require the diabetes patient to periodically self-administer insulin in public locations, such as places of employment or restaurants. The required manipulation of the standard prior art hypodermic syringe and vial can be inconvenient and embarrassing in these public environments.

Medication delivery pens have been developed to facilitate the self-administration of medication. One prior art medication delivery pen includes a vial holder into which a vial of insulin or other medication may be received. The vial holder is an elongate generally tubular structure with proximal and distal ends. The distal end of the prior art vial holder includes mounting means for engaging a double-ended needle cannula. The proximal end also includes mounting means for engaging a driver and dose setting apparatus as explained further below. A disposable vial for use with the prior art vial holder includes a distal end having a pierceable elastomeric seal that can be pierced by one end of a double-ended needle cannula. The proximal end of this prior art vial includes a plunger slidably disposed in fluid tight engagement with the cylindrical wall of the vial. This prior art medication delivery pen is used by inserting the vial of medication into the vial holder. A prior art pen body then is connected to the proximal end of the vial holder. The pen body includes a dose setting apparatus for designating a dose of medication to be delivered by the pen and a driving apparatus for urging the plunger of the vial distally for a distance corresponding to the selected dose.

The user of the pen mounts a prior art double-ended needle cannula to the distal end of the vial holder such that the proximal point of the needle cannula pierces the elastomeric seal on the vial. The patient then selects a dose and operates the pen to urge the plunger distally to deliver the selected dose. The dose selecting apparatus returns to zero upon injection of the selected dose with this prior art medication delivery pen. The patient then removes and discards the needle cannula, and keeps the prior art medication delivery pen in a convenient location for the next required medication administration. The medication in the vial will become exhausted after several such administrations of medication. The patient then separates the vial holder from the pen body. The empty vial may then be removed and discarded. A new vial can be inserted into the vial holder, and the vial holder and pen body can be reassembled and used as explained above.

The above-described medication delivery pen is effective and much more convenient for self-administration of medication than hypodermic syringes using separate medication vials. However, current medication delivery pens must be used with vials having a predefined length and must be disassembled for these vials to be loaded into the medication delivery pen. As a result, users with impaired fine motor skill and vision have found it difficult to disassemble and load vials into such medication delivery pens. Since it is particularly common among patients with diabetes to have complications of the disease causing impaired motor skills, even more of a need has been found to address this problem. Hence, it is necessary to provide a medication delivery pen having a vial retainer that provides for improved versatility by allowing the user to use a plurality of different length vials in the medication delivery pen. This provides the user with the freedom to choose the type of medicament vial or insulin type more freely while using the same injection prefill syringe or medication delivery pen.

In addition, it would be desired to have a device that is easier and more intuitive to use than the current medication delivery pens and that also prevents the user from removing the vial from the medication delivery pen after use, which is important to prevent reuse of a contaminated device. It is also preferable to have a device that allows for the loading of the vial without complete disassembly of the medication delivery pen and with a fail-safe loading system that prevents the user from incorrectly loading the vial into the medication delivery pen.

SUMMARY OF THE INVENTION

The present invention relates to a medication delivery pen having a vial retainer that addresses the above-identified problems. In particular, the vial retainer includes a side opening having flexible snap wings that spread to receive and retain a standard or threaded vial within the vial retainer. The vial retainer also includes an improved means of attaching the vial retainer to a pen injector body, using a cam and cam follower design together with a ratcheting mechanism to prevent removal of the vial from the medication delivery pen. Alternatively, a release mechanism could be used so that the vial may be removed from the medication delivery pen.

Another feature of the present invention is a medication delivery pen having a vial retainer for receiving and holding the vial including an opening for receiving the vial defined by a pair of flexible snap wings.

BRIEF DESCRIPTION OF THE DRAWINGS

FIG. 2 is a partial cross-sectional view of the pen injector body of the medication delivery pen shown in FIG. 1 along line A—A.

FIGS. 3–4 are perspective views showing the vial being loaded into a vial retainer of the medication delivery pen shown in FIG. 1.

FIG. 8 is a perspective view of the medication delivery pen shown in FIG. 5 with the vial retainer rotated into the ready to use position.

FIG. 9 is a cross-sectional view of the medication delivery pen shown in FIG. 8 along line A—A.

FIG. 13 is an exploded perspective view of yet another medication delivery pen including a linear ratchet interface between the vial retainer and the pen injector body.

FIG. 14 is a cross-sectional view of the medication delivery pen shown in FIG. 13 along line A—A.

DETAILED DESCRIPTION OF THE INVENTION

Figure 1:
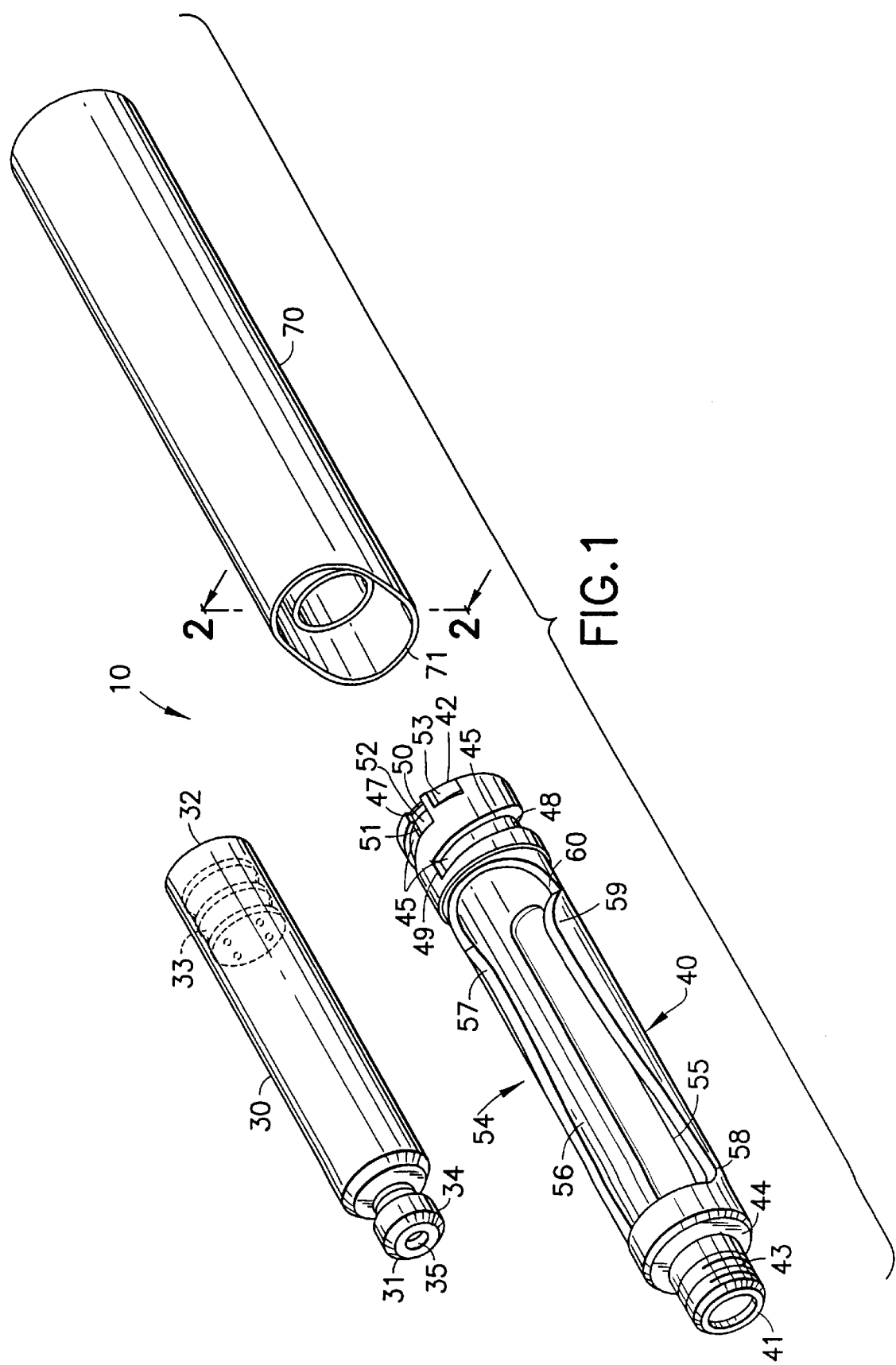
FIG. 1 is an exploded perspective view of a medication delivery pen according to the present invention.

FIG. 1 is a perspective view of the medication delivery pen 10 having a pen injector body 70 and a vial retainer 40 that receives a standard vial 30 or alternatively a threaded vial (described below). Vial 30 includes a distal end 31 and an open proximal end 32 with a septum 35 held on to distal end 31 by a cap 34. Vial 30 also includes an axially slidable piston 33 that seals open proximal end 32 and is moveable to dispense medication from vial 30 during an injection procedure performed by medication delivery pen 10.

Vial retainer 40 includes a distal end 41 and a proximal end 42, wherein distal end 41 further includes a set of needle attachment threads 43 and extends from a vial retainer shoulder 44. Needle attachment threads 43 are intended for receiving a standard pen needle having matching threads within its hub. Vial retainer 40 also includes means for attaching vial retainer 40 to pen injector body 70. These attachment means include a plurality of cam tracks 45 on an outer surface 46 of vial retainer 40. Each cam track 45 is defined by an axial section 47 and a radial section 48 extending around the circumference of vial retainer 40. Radial section 48 has a slope that varies from axial section 47 to an end wall 49 which provides for sufficient force to attach vial retainer 40 to pen injector 70, as described below. Cam track 45 also includes an axial protrusion 50 in axial section 47 and a radial protrusion 51 in radial section 48, which together define a shipping/loading pocket 52 there between. Proximal end 42 of vial retainer 40 also includes a plurality of ratchet fingers 53 extending inwardly.

Vial retainer 40 also includes a center portion 54 located between distal end 41 and proximal end 42 having a viewing window 55 on one side and a larger side opening 56 on the other side. Larger side opening 56 is defined by a pair of flexible snap wings 57 that are both ear-shaped having a narrow portion 58 near the distal end of opening 56 and a wider portion 59 near the proximal end of opening 56. Opening 56 also includes a stress relief 60 at the proximal end of wing 57 near wide portion 59. Flexible snap wings 57 are designed to spread apart to accept and retain vial 30 within opening 56 and within vial retainer 40, as further described below.

FIG. 2 is a cross-section view of pen injector body 70 which includes an outer sleeve 72 and an inner sleeve 73 at its distal end 71. Inner sleeve 73 is connected to outer sleeve 72 by an inner wall 74 and outer sleeve 72 includes an plurality of cam followers 75 on its inside surface 76. Inner sleeve 73 is spaced from inside surface 76 of outer sleeve 72 and includes a distal edge 77 and a radial ratchet 78 on an outside surface 79 located adjacent to inner wall 74 and begins at a distance from distal edge 77 near cam followers 75 on inside surface 76.

FIGS. 3 and 4 are perspective views of vial retainer 40 showing the process of loading vial 30 through side opening 56 and into vial retainer 40. In particular, FIG. 4 shows the action of spreading the pair of flexible snap wings 57 to accept and retain vial 30 within side opening 56. In addition, it is clearly shown that distal end 31 of vial 30 is inserted into narrow portion 58 of opening 56 so that cap 34 and septum 35 are received in distal end 41 of vial retainer 40. As vial 30 is fully inserted into vial retainer 40 a shoulder 37 on vial 30 is moved into contact with vial retainer shoulder 44 on vial retainer 40 as clearly shown in FIG. 5 where medication delivery pen 10 has been assembled into a shipping/loading position and vial 30 has been fully loaded and retained within side opening 56 of vial retainer 40.

Figure 5:
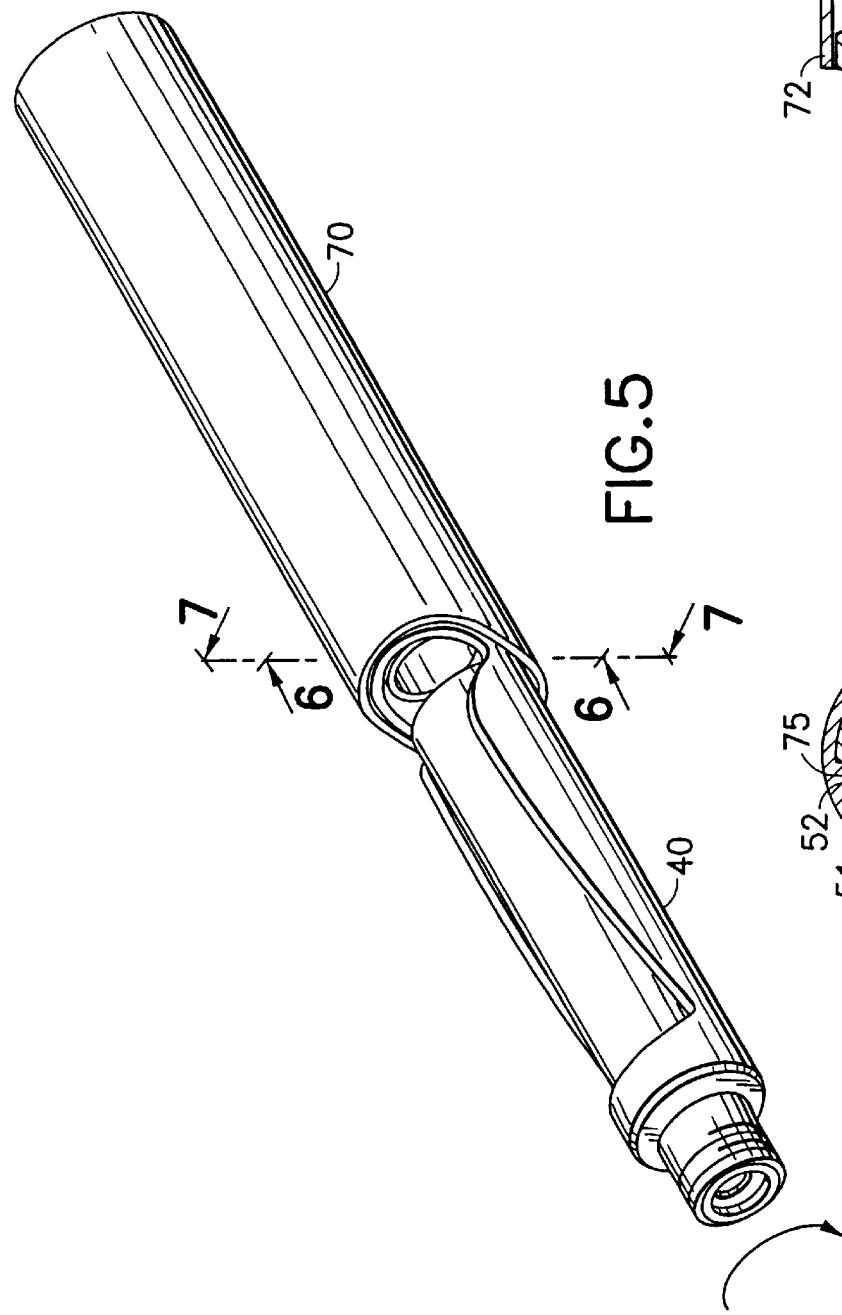
FIG. 5 is a perspective view of the medication delivery pen shown in FIG. 1 assembled in a shipping position with the vial fully loaded into the vial retainer.
Figure 7:
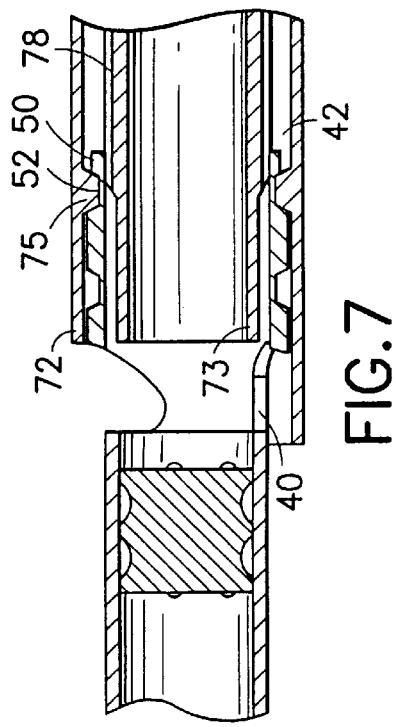
FIG. 7 is a cross-sectional view of the medication delivery pen shown in FIG. 5 along line B—B.
Figure 6:
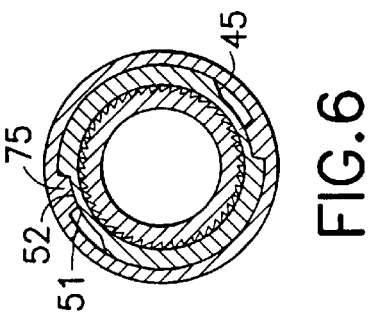
FIG. 6 is a cross-sectional view of the medication delivery pen shown in FIG. 5 along line A—A.

FIG. 6 is a cross-sectional view along the line A—A shown in FIG. 5 that more clearly shows the position of each cam follower 75 in each cam track 45 and, more particularly that each cam follower 75 is positioned in a shipping/loading pocket 52 defined by radial protrusion 51 shown in FIG. 6 and axial protrusion 50 shown in FIG. 7.

FIG. 7 is a partial longitudinal cross-sectional view along lines B—B. FIG. 6 also shows relative positions of outer sleeve 72, inner sleeve 73 having radial ratchet 78 and proximal end 42 of vial retainer 40 there between.

As shown in FIG. 5 vial retainer 40 is then rotated in the direction of Arrow while hold pen injector body 70 such that each cam follower 75 leaves shipping/loading pocket 52 so to travel through radial section 48 of each cam track 45 until vial retainer 40 reaches a ready to use position, as shown in FIG. 8. In the ready to use position each cam follower 75 has moved through a portion of radial section 48 having a predefined variable slope to provide sufficient axial force between distal edge 77 of inner sleeve 73 within pen injector body 70 and proximal end 32 of vial 30 to fully seat vial shoulder 37 on vial retainer shoulder 44 within vial retainer 40. Interaction between distal edge 77 on inner sleeve 73 is with proximal end 32 of vial 30 is more clearly shown in FIG. 10, described below.

FIG. 9 is a cross-sectional view of medication delivery pen 10 shown in FIG. 8 along line A—A and more clearly shows interaction between ratchet fingers 53 on proximal end 42 of vial retainer 40 and radial ratchet 78 on inner sleeve 73, which together prevent backwards rotation or movement of cam followers 75 backward within cam track 45. Therefore, ratchet fingers 53 and radial ratchet 78 ensure that the force being applied by distal edge 77 on proximal end 32 of vial 30 is constant and sufficient to retain vial 30 in position.

Figure 10:
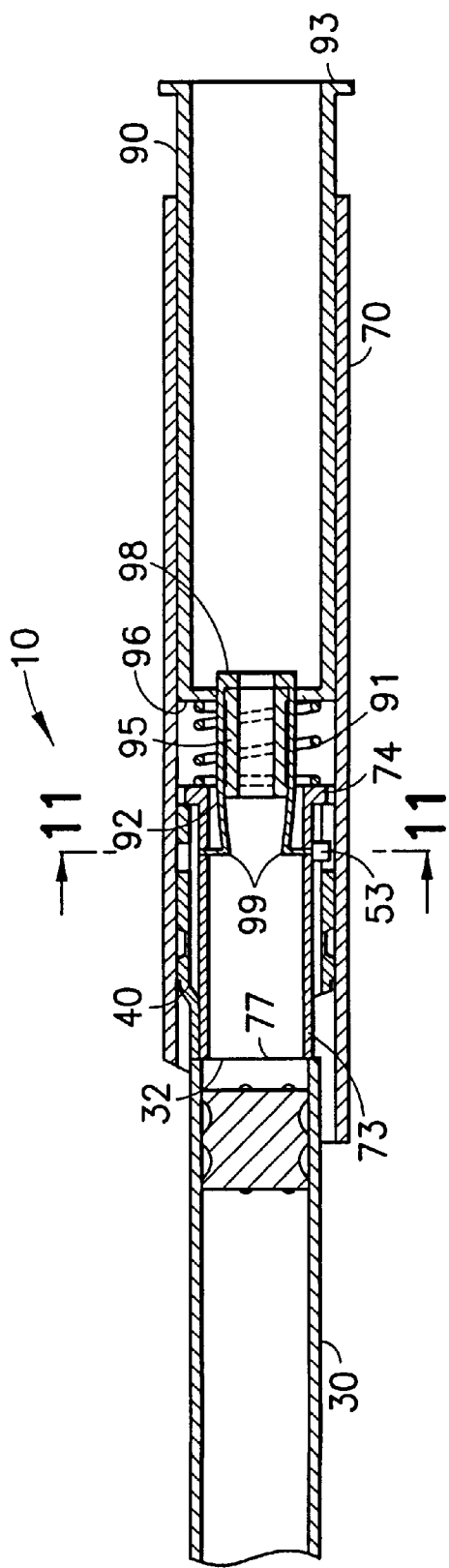
FIG. 10 is a cross-sectional view of an alternative medication delivery pen including a release mechanism.

FIG. 10 is a cross-sectional view of an alternative medication delivery pen 10 having a release mechanism to release the forces being applied by distal edge 77 of inner sleeve 73 against proximal end 32 of vial 30. The release mechanism includes a release plunger 90, spring 91 and an expandable collet 92. The release plunger 90 includes a thumb flange 93 extending from its main body which includes a distal end extension 95 and a shoulder 96. Spring 91 is held between shoulder 96 and inner wall 74 of pen injector body 70 and extension 95 of release plunger 90 is received within a proximal end 98 of expandable collet 92. Expandable collet 92 also includes a plurality of release fingers 99 extending from a distal end 97.

Figure 11:
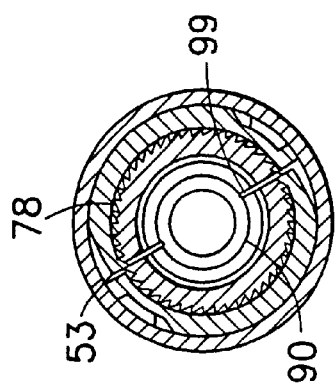
FIG. 11 is a cross-sectional view of the medication delivery pen shown in FIG. 10 along line A—A.

FIG. 11 is a cross-sectional view along line A—A showing ratchet fingers engaged in radial ratchet 78 as they would be, for example, when medication delivery pen 10 is in the ready to use position as described above. In addition, FIG. 11, shows the position of release fingers 99 and there corresponding ratchet fingers 53. A medication delivery pen 10 incorporating this release mechanism will provide for release of the medication delivery pen 10 from its ready by position so that vial 30 could be removed from vial retainer 45 to use moving release plunger 90 in the distal direction against the force of spring 91 to move extension 95 into expandable collet 92 and thereby expand collet 92 to force release fingers 99 to disengage ratchet fingers 53 from radial ratchet 78. This process would then allow rotation of vial retainer 40 in the opposite direction back to its shipping/loading position at which vial 30 could be removed from side opening 56.

Figure 12:
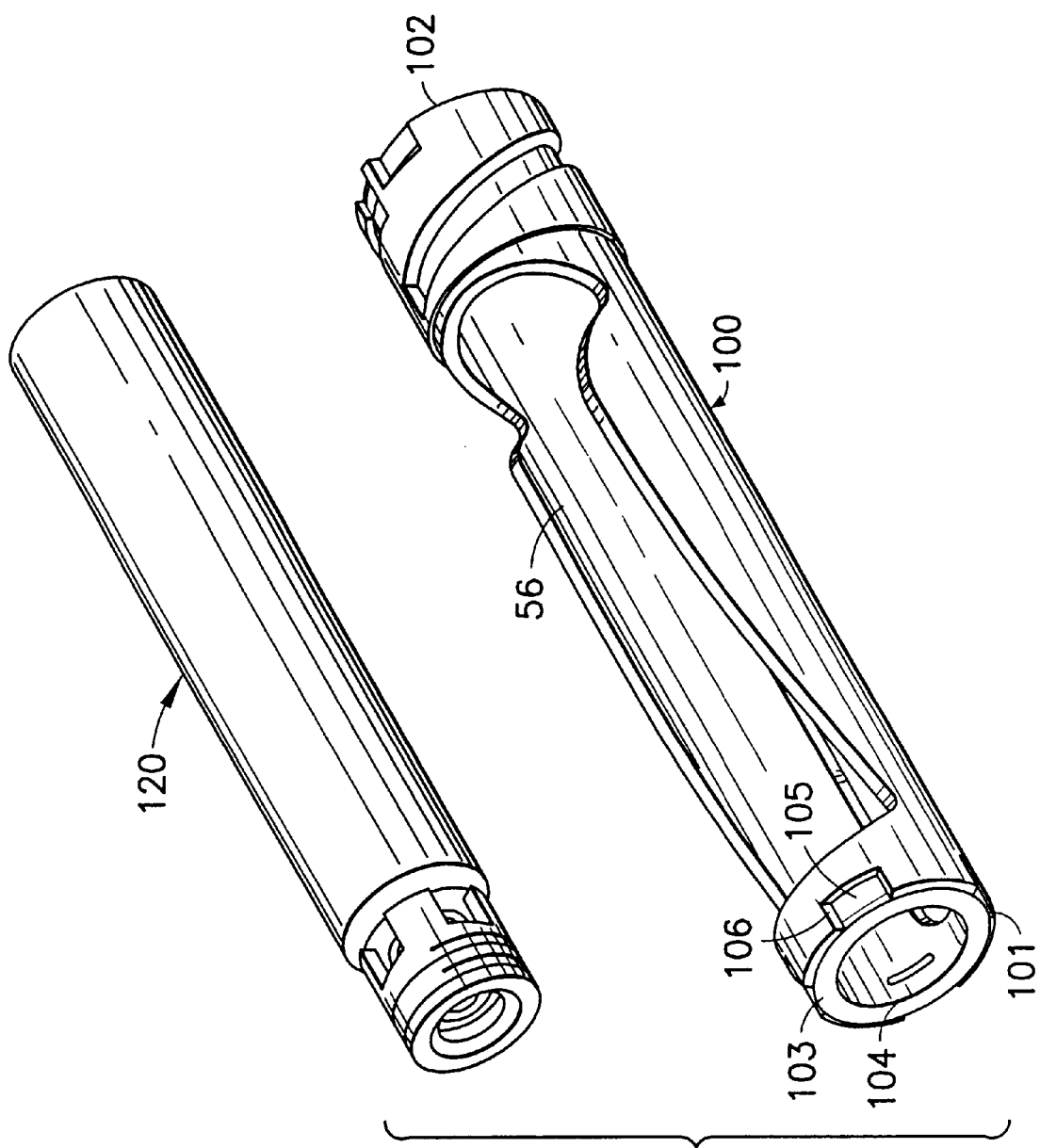
FIG. 12 is an exploded perspective view of an alternative vial retainer for use with a threaded vial.

FIG. 12 is a perspective view of an alternative vial retainer 100 having a distal end 101 and a proximal end 102, wherein distal end 101 does not include threads as in the earlier embodiment. Threadless vial retainer 100 includes a front retainer clip 103 having a ring 104 and a plurality of fingers 105 extending therefrom. As an example, retainer clip 103 can be made from stainless steal or polycarbonate and vial retainer 100 can be made of polypropylene. In any event, it is important for retainer clip 103 to be made from a material that is less flexible that the material used to make wings 57 on vial retainer 100. Each of the fingers 105 are received by one of a plurality of openings 106 around the circumference of distal end 101. threadless vial retainer 100 would be used with a threaded vial 120 having threads internally molded or attached thereto, as shown in FIG. 12. Vial 120 would be inserted into side opening 56 and retained with threadless retainer 100, as described above in the earlier embodiment.

FIGS. 13 and 14 show another alternative medication delivery pen 200 having different means for attaching a vial retainer 240 to a pen injector body 270. All the other features and characteristics of medication delivery pen 200 would be the same as the above described medication delivery pen 10. The means for attached vial retainer 240 to pen injector body 270 include a set of ratchet teeth 253 at a proximal end 242 of vial retainer 240 that meet with a set of linear mating ratchet teeth within an inside surface 276 of an outer sleeve 272 near a distal end 271 of pen injector body 270. Linear mating teeth are 279. Vial retainer 240 would be attached to pen injector body 270 by insert proximal end 242 of vial retainer 240 into distal end 271 of pen injector body 270 until sufficient force has been applied by a distal edge 277 of an inner sleeve 273 within pen injector body 270 against proximal end 32 of vial 30 at which point linear ratchet teeth 253 would be properly engaged with linear mating ratchet teeth 279, thereby firmly attaching vial retainer 240 to pen injector body 270.

While the present invention has been described with respect to a preferred and a number of alternative embodiments, it is apparent that various changes can be made without departing from the scope of the invention as defined by the appended claims.

What is claimed is:

1. A medication delivery pen comprising:

a pen injector body having a distal end;

a vial retainer for receiving and holding a vial and having a distal end and a proximal end;

means for attaching said vial retainer to said pen injector body in either a shipping/loading position or a ready-to-use position,
wherein the vial can be loaded into said vial retainer when said attaching means is in the shipping/loading position, and
wherein said vial retainer and said pen injector body are ready to perform an injection when said attaching means is in the ready-to-use position; and means for preventing said attaching means from moving from said ready-to-use position to said shipping/loading position said preventing means including:
a plurality of ratchet fingers on said vial retainer; and
a ratchet on said pen injector body that mates with said ratchet fingers to prevent said attaching means from moving from said ready-to-use position to said shipping/loading position.

2. A medication delivery pen according to claim 1, wherein said vial retainer further includes means for attaching a pen-needle to said distal end.

3. A medication delivery pen according to claim 1, wherein said means for attaching includes:

a plurality of cam followers within said pen injector body; and a plurality of cam tracks on said vial retainer, wherein said cam tracks have a predefined variable slope that functions to provide a predefined axial force between said vial retainer and said pen injector body.

4. A medication delivery pen according to claim 3, wherein each cam track includes an axial section and a radial section, said radial section having a variable slope and a radial protrusion and said axial section having an axial protrusion, wherein a loading pocket is formed within said cam track between said axial protrusion and said radial protrusion.

5. A medication delivery pen according to claim 3, further comprising a release mechanism for releasing said preventing means to release said attaching means from the ready-to-use position to return to the shipping/loading position.

6. A medication delivery pen according to claim 5, wherein said release mechanism includes a finger that interacts with said ratchet fingers on said vial retainer to disengage said ratchet fingers from said ratchet within said pen injector body so that each cam follower can move back down its respective cam track to allow said vial to be removed from said vial retainer when said attaching means has been returned to the shipping/loading position.

7. A medication delivery pen according to claim 6, wherein said release mechanism further includes a release plunger having an extension that is received by an expandable collet, such that when said release plunger is pushed in a distal direction said collet expands to thereby push said finger into engagement with said ratchet fingers on said vial retainer.

\* \* \* \* \*